United States Patent
Rampf et al.

(10) Patent No.: US 7,102,046 B2
(45) Date of Patent: Sep. 5, 2006

(54) PROCESS FOR THE ARYLATION OF OLEFINS

(75) Inventors: Florian Rampf, Köln (DE); Markus Eckert, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 162 days.

(21) Appl. No.: 10/305,880

(22) Filed: Nov. 27, 2002

(65) Prior Publication Data

US 2003/0105353 A1 Jun. 5, 2003

(30) Foreign Application Priority Data

Dec. 3, 2001 (DE) .............................. 101 59 270

(51) Int. Cl.
- *C07C 2/02* (2006.01)
- *C07C 2/54* (2006.01)
- *C07C 2/64* (2006.01)
- *C07C 2/68* (2006.01)
- *C07C 2/66* (2006.01)

(52) U.S. Cl. ..................... 585/502; 585/501; 585/506; 585/601; 585/600; 562/862

(58) Field of Classification Search ............... 562/862; 585/502, 501, 506, 601, 600
See application file for complete search history.

(56) References Cited

OTHER PUBLICATIONS

Zapf et al, Chem Eur J. 2001, 7(3) pp. 2908-2915.*
Litke et al, J. Am Chem Soc. 2001, 123 pp. 6989-7000.*

Chem. Eur. J. (month unavailable) 2001, 7, No. 13, pp. 2908-2915, Alexander Zapf and Matthias Beller, "Palladium Catalyst Systems for Cross-Coupling Reactions of Aryl Chlorides and Olefins".

J. Am. Chem. Soc., (month unavailable) 2001, 123, pp. 6989-7000, Adam F. Littke and Gregory C. Fu, "A Versatile Catalyst for Heck Reactions of Aryl Chlorides and Aryl Bromides under Mild Conditions".

Christoph Gürtler and Stephen L. Buchwald: "A Phosphane Free Catalyst System for the Heck Acrylation of Disubstituted Alkenes: Application to the Synthesis of Trisubstituted Olefins" Chem. Eur. J., Bd. 5, Nr. 11, 1999, Seiten 3107-12, XP00224412 das ganze Dokument.

Sabine Berteina, Sabastian Wendeborn, Wofgang K. -D. Brill and Allain De Mesmaeker; "Pd mediated C—C Bond Formation with Olefins and Acetylenes on Solid Support: A Scope and Limitation Study" SYNLETT Bd. 6, 1998, Seiten 676-8, XP002244143 Tabelle 3.

Adam F. Littke and Gregory C. Fu: "A versatile catalyst for Heck reactions of aryl chlorides and aryl bromides under mild conditions" Journal of the American Chemical Society, American Chemical Society, Washington DC, US Bd. 123, Nr. 29, 2001 Seiten 6989-7000, XP002236859 ISSN: 0002-7863 in der Anmmeldung erwähnt das ganze Dokument.

* cited by examiner

*Primary Examiner*—Elvis O. Price
(74) *Attorney, Agent, or Firm*—Jennifer R. Seng

(57) ABSTRACT

The present invention relates to a process for the arylation of olefins by reaction of haloaromatics or arylsulfonates with olefins in the presence of a palladium catalyst, a bulky nitrogen base and a salt.

23 Claims, No Drawings

PROCESS FOR THE ARYLATION OF OLEFINS

BACKGROUND OF THE INVENTION

1. Field of the Invention

The present invention relates to a process for the arylation of olefins by reaction of haloaromatics or arylsulfonates with olefins in the presence of a palladium catalyst, a bulky nitrogen base and a salt.

2. Brief Description of the Prior Art

Many aryl olefins have great industrial importance as fine chemicals, UV absorbers, starting materials for polymers and intermediates for active compounds.

The preparation of arylolefins is frequently carried out by means of palladium-catalyzed coupling of iodoaromatics or bromoaromatics, and to a lesser extent chloroaromatics or arylsulfonates, with olefins. Owing to the high price of iodoaromatics and bromoaromatics and the large amounts of waste product caused by the high molar masses, their use on an industrial scale is disadvantageous. However, the more readily available and therefore more attractive chloroaromatics have a comparatively low reactivity.

Zapf and Beller (Chem. Eur. J. 2001, 7, 2908) describe, inter alia, the palladium-catalyzed reaction of chloroaromatics with olefins at temperatures of 160° C. with addition of 20 mol % of quaternary ammonium salts in the presence of a base. Catalyst turnover numbers (TONs) of 850–1000 are achieved in 24 hours.

However, disadvantages of this process are the high quaternary ammonium salt requirements and the low catalyst turnover frequencies (TOFs) of a maximum of 42 per hour.

Littke and Fu (J. Am. Chem. Soc. 2001, 123, 6989) describe a process in which chloroaromatics are reacted with olefins at room temperature using palladium-dibenzylideneacetone ($[Pd_2(dba)_3]$) and tri-tert-butylphosphine in the presence of dicyclohexylmethylamine. However, large amounts of palladium catalyst are required for the process described, which makes its industrial application uneconomical.

There was therefore a need to develop a process which makes it possible for haloaromatics, in particular chloroaromatics, to be coupled with olefins in an efficient way.

SUMMARY OF THE INVENTION

We have now found a process for preparing arylolefins, which is characterized in that aromatic compounds of the general formula (I),

where n is one or two and

Ar is a substituted or unsubstituted aromatic radical and

X are each, independently of one another, chlorine, bromine, iodine or a sulphonate, are reacted with olefins which bear at least one hydrogen atom on the double bond in the presence of a palladium catalyst, at least one bulky nitrogen base and at least one salt and in the presence or absence of solvents.

DETAILED DESCRIPTION OF THE INVENTION

The invention is described more fully below with particular reference to the preferred elements. It may be pointed out at this juncture that any combinations of preferred ranges are encompassed by the invention.

For the purposes of the invention, Ar is, by way of example and preferably, a carbocyclic aromatic radical having from 6 to 24 framework carbon atoms or a heteroaromatic radical having from 5 to 24 framework carbon atoms in which no, one, two or three framework carbon atom(s) per ring, but at least one framework carbon atom in the total molecule, can be replaced by heteroatoms selected from the group consisting of nitrogen, sulphur and oxygen. Furthermore, the carbocyclic aromatic radicals or heteroaromatic radicals may be substituted by up to five identical or different substituents per ring selected from the group consisting of hydroxy, fluorine, nitro, cyano, free or protected formyl, $C_1$–$C_{12}$-alkyl, $C_5$–$C_{14}$-aryl, $C_6$–$C_{15}$-arylalkyl, —PO—[($C_1$–$C_8$)-alkyl]$_2$, —PO—[($C_5$–$C_{14}$)-aryl]$_2$, —PO—[($C_1$–$C_8$)-alkyl)($C_5$–$C_{14}$)-aryl)], tri($C_1$–$C_8$-alkyl)siloxyl and radicals of the general formula (II),

where, independently of one another,

A is absent or is a $C_1$–$C_8$-alkylene radical and

B is absent or is oxygen, sulphur or $NR^1$, where $R^1$ is hydrogen, $C_1$–$C_8$-alkyl, $C_6$–$C_{15}$-arylalkyl or $C_5$–$C_{14}$-aryl and D is a carbonyl group and K is $R^2$, $OR^2$, $NHR^3$ or $N(R^3)_2$, where $R^2$ is $C_1$–$C_8$-alkyl, $C_6$–$C_{15}$-arylalkyl, $C_1$–$C_8$-haloalkyl or $C_5$–$C_{14}$-aryl and $R^3$ are each, independently of one another, $C_1$–$C_8$-alkyl, $C_6$–$C_{15}$-arylalkyl or $C_6$–$C_{14}$-aryl or the moiety $N(R^3)_2$ is a cyclic amino radical, and radicals of the general formulae (IIIa–e)

where A, B, K and $R^2$ are as defined above and W is OH, $NH_2$, or OM, where M can be an alkali metal ion, half an equivalent of an alkaline earth metal ion, an ammonium ion or an organic ammonium ion.

For the purposes of the invention, alkyl or alkylene or alkoxy are each, independently of one another, a straight-chain, cyclic, branched or unbranched alkyl or alkylene or alkoxy radical which may be further substituted by $C_1$–$C_4$-alkoxy radicals. The same applies to the alkyl part of an arylalkyl radical.

In all contexts, $C_1$–$C_6$-alkyl is preferably methyl, ethyl, n-propyl, isopropyl, n-butyl, tert-butyl, n-pentyl, cyclohexyl or n-hexyl, $C_1$–$C_8$-alkyl may also be, for example, n-heptyl, n-octyl or isooctyl, $C_1$–$C_{12}$-alkyl may also be, for example, n-decyl and n-dodecyl and $C_1$–$C_{20}$-alkyl may also be n-hexadecyl and n-octadecyl.

In all contexts, $C_1$–$C_4$-alkylene is preferably methylene, 1,1-ethylene, 1,2-ethylene, 1,1-propylene, 1,2-propylene, 1,3-propylene, 1,1-butylene, 1,2-butylene, 2,3-butylene and 1,4-butylene, $C_1$–$C_8$-alkylene may also be 1,5-pentylene, 1,6-hexylene, 1,1-cyclohexylene, 1,4-cyclohexylene, 1,2-cyclohexylene and 1,8-octylene.

In all contexts, $C_1$–$C_4$-alkoxy is preferably methoxy, ethoxy, isopropoxy, n-propoxy, n-butoxy and tert-butoxy, $C_1$–$C_8$-alkoxy may also be cyclohexyloxy.

The general designation aryl as substituent encompasses carbocyclic radicals and heteroaromatic radicals in which no, one, two or three framework atoms per ring, but at least one framework atom in the overall radical, are heteroatoms selected from the group consisting of nitrogen, sulphur and oxygen. $C_5$–$C_{10}$-aryl is, by way of example and preferably, phenyl, pyridyl, o-, m-, or p-tolyl, $C_5$–$C_{14}$-aryl may also be anthracenyl.

The same applies to the aryl part of an arylalkyl radical. $C_6$–$C_{15}$-arylalkyl is, by way of example and preferably, benzyl.

For the purposes of the invention, haloalkyl and fluoroalkyl are each, independently of one another, a straight-chain, cyclic, branched or unbranched alkyl radical which may be monosubstituted, polysubstituted or fully substituted by halogen atoms selected independently from the group consisting of fluorine, chlorine and bromine or by fluorine.

In all contexts, $C_1$–$C_8$-haloalkyl is, by way of example and preferably, trifluoromethyl, trichloromethyl, 2,2,2-trifluoroethyl, pentafluoroethyl or nonafluorobutyl, $C_1$–$C_8$-fluoroalkyl may be trifluoromethyl, 2,2,2-trifluoroethyl, pentafluoroethyl or nonafluorobutyl.

Protected formyl is a formyl radical which has been protected by conversion into an aminal, acetal or a mixed aminal-acetal, with the aminals, acetals and mixed aminal-acetals being able to be acyclic or cyclic.

Protected formyl is, by way of example and preferably, a 1,1-(2,5-dioxy)cyclopentylene radical.

In the process of the invention, preference is given to using aromatic compounds of the general formula (I) in which n=one and Ar is a substituted or unsubstituted aromatic radical selected from the group consisting of phenyl, naphthyl, phenanthrenyl, anthracenyl, fluorenyl, pyridinyl, oxazolyl, thiophenyl, benzofuranyl, benzothiophenyl, dibenzofuranyl, dibenzothiophenyl, furanyl, indolyl, pyridazinyl, pyrazinyl, pyrimidinyl, triazolyl and quinolinyl which may also be further substituted by no, one, two or three radicals per ring which are selected independently from the group consisting of fluorine, nitro, cyano, di($C_1$–$C_6$-alkyl)amino, $C_1$–$C_6$-alkyl, $C_5$–$C_{10}$-aryl, $C_1$–$C_8$-fluoroalkyl, $C_1$–$C_8$-fluoroalkoxy, $C_1$–$C_8$-alkoxy, CO($C_1$–$C_4$-alkyl), COO—($C_1$–$C_6$)-alkyl, —CON($C_1$–$C_6$-alkyl)$_2$, and X is chlorine, bromine, iodine, trifluoromethanesulphonyloxy or nonafluorobutanesulphonyloxy.

In the process of the invention, particular preference is given to using aromatic compounds of the general formula (I) in which n=one and Ar is a phenyl radical which may be further substituted by no, one, two or three radicals selected independently from the group consisting of fluorine, cyano, $C_1$–$C_4$-alkyl, $C_1$–$C_4$-alkoxy, trifluoromethyl, trifluoromethoxy, acetyl, COO—($C_1$–$C_6$)-alkyl, —CON($C_1$–$C_6$-alkyl)$_2$ and X is chlorine or bromine.

Very particular preference is given to using the following compounds: p-trifluoromethylchlorobenzene, o-trifluoromethylchlorobenzene, m-trifluoromethylchlorobenzene, 3,5-bis(trifluoromethyl)chlorobenzene, o-cyanochlorobenzene, p-chlorobenzaldehyde.

Palladium catalysts used are, by way of example and preferably, palladium complexes.

Palladium complexes can, for example, be generated from palladium compounds and suitable ligands in the reaction solution, or can be used in the form of previously isolated palladium complexes.

Isolated palladium complexes suitable for the process of the invention are, for example, palladium complexes containing phosphorus compounds such as phosphines, phosphites, phosphonites or mixtures thereof, preferably phosphines, as ligands.

As palladium complexes which can contain phosphorus compounds as ligands, use is made, by way of example and preferably, of complexes of the general formula (IV), $$[PdL_2An_2] \qquad (IV)$$

where

L is in each case a monophosphorus compound or $L_2$ as a whole represents a diphosphorus compound and An is an anion, preferably chloride, bromide, iodide, acetate, propionate, allyl or cyclopentadienyl, or complexes of the general formula (IVb)

$$[PdL_n] \qquad (IVb)$$

where n is 2, 3 or 4 and

L is in each case a monophosphorus compound or can represent half an equivalent of a diphosphorus compound.

Monophosphorus compounds are, by way of example and preferably, compounds of the general formula (Va)

$$P(E\text{—}R^4)_3 \qquad (Va)$$

where

E are each, independently of one another and independently of $R^4$, absent or oxygen and the radicals $R^4$ are each, independently of one another, $C_1$–$C_8$-alkyl or unsubstituted phenyl, naphthyl or ferrocenyl or phenyl, naphthyl or ferrocenyl substituted by one, two or three radicals $R^5$, where $R^5$ is $C_1$–$C_8$-alkyl, $C_1$–$C_8$-alkoxy, chlorine, fluorine, N($C_1$–$C_6$-alkyl)$_2$, $CO_2$—($C_1$–$C_6$-alkyl), —CON($C_1$–$C_6$-alkyl)$_2$, cyano or CO($C_1$–$C_6$-alkyl).

Particularly preferred monophosphorus compounds are those of the general formula (Va) in which E is absent and $R^4$ are each, independently of one another, $C_1$–$C_8$-alkyl or unsubstituted phenyl or naphthyl or ferrocenyl or phenyl or naphthyl or ferrocenyl substituted by one, two or three radicals $R^5$, where $R^5$ is $C_1$–$C_8$-alkyl, $C_1$–$C_8$-alkoxy, chlorine or fluorine.

Very particular preference is given to monophosphorus compounds of the general formula (Va) in which E is absent and two or three of the radicals $R^4$ are each, independently of one another, $C_1$–$C_8$-alkyl and no or one radical $R^4$ is unsubstituted phenyl or naphthyl or phenyl or naphthyl substituted by one, two or three radicals $R^5$, where $R^5$ is $C_1$–$C_8$-alkyl, $C_1$–$C_8$-alkoxy, chlorine or fluorine.

Even more preferred monophosphorus compounds are tri(tert-butyl)phosphine, phenyldi(tert-butyl)phosphine and ferrocenyldi(tert-butyl)phosphine.

Diphosphorus compounds can be, by way of example and preferably, compounds of the general formula (Vb), $$(R^6\text{-}E)_2P\text{-}E\text{-}Z\text{-}E\text{-}P(E\text{-}R^6)_2 \qquad (Vb)$$

where

E are each, independently of one another and independently of $R^6$ and Z, absent or oxygen and the radicals $R^6$ are each, independently of one another, $C_1$–$C_8$-alkyl or phenyl, naphthyl or heteroaryl having from 5 to 12 framework carbon atoms which may be unsubstituted or substituted by one, two or three radicals $R^7$, where $R^7$ are selected independently from the group consisting of $C_1$–$C_8$-alkyl, $C_1$–$C_8$-alkoxy, fluorine and cyano and Z is an unsubstituted or substituted radical selected from the group consisting of $C_1$–$C_4$-alkylene, 1,2-phenylene, 1,3-phenylene, 1,2-cyclohexyl, 1,1'-ferrocenyl, 1,2-ferrocenyl, 2,2'-(1,1'-binaphthyl) and 1,1'-biphenyl.

Preferred diphosphorus compounds are 1,3-bis(diisopropylphosphino)propane, 1,4-bis(diisopropylphosphino)butane, 2,2'-bis(diphenylphosphino)-1,1'-binaphthyl.

Preference is given to using complexes which contain monophosphorus compounds as ligands.

Preferred isolated palladium complexes are bis(tri-t-butylphosphine)palladium(II) dichloride, bis(di-tert-butylphenylphosphine)palladium(II) dichloride, bis(di-tert-butylferrocenylphosphine)palladium(II) dichloride, tricyclohexylphosphinepalladium(0)-diallyl ether complex, bistricyclohexylphosphinepalladium(0).

In the process of the invention, palladium complexes generated in the reaction solution from palladium compounds and ligands are preferred as palladium catalysts.

As palladium compounds, it is possible to use, by way of example and preferably, $Pd_2$(dibenzylideneacetone)$_3$ or allylpalladium chloride or bromide or compounds of the general formula (VIa),

$$Pd(Y^1)_2 \quad\quad\quad (VIa)$$

where $Y^1$ is an anion, preferably chloride, bromide, acetate, propionate, nitrate, methanesulphonate, trifluoromethanesulphonate, acetylacetonate, allyl or cyclopentadienyl, or palladium compounds of the general formula (VIb)

$$Pd(Y^2)_2(L^1)_2 \quad\quad\quad (VIb)$$

where $Y^2$ is an anion, preferably chloride, bromide, acetate, methanesulphonate, nonafluorobutanesulphonate or trifluoromethanesulphonate, tetrafluoroborate or hexafluorophosphate and $L^1$ are each a nitrile, preferably acetonitrile, benzonitrile or benzyl nitrile, or an olefin, preferably cyclohexene or cyclooctene, or $(L^1)_2$ as a whole represents a diolefin, preferably norbornadiene or 1,5-cyclooctadiene, or palladium compounds of the general formula (VIc)

$$M_2[Pd(Y^3)_4] \quad\quad\quad (VIc),$$

where $Y^3$ is a halide, preferably chloride or bromide, and

M is lithium, sodium, potassium, ammonium or organic ammonium.

Preferred palladium compounds are palladium(II) acetate, palladium(II) chloride, palladium(II) bromide, palladium(II) propionate, palladium(II) acetylacetonate, lithium, sodium or potassium tetrachloropalladate, bisbenzonitrilepalladium(II) chloride, bisacetonitrilepalladium(II) chloride.

Preference is given to using the phosphorus compounds of the general formulae (Va) and (Vb) as ligands for the generation of palladium complexes in the reaction solution, with monophosphorus compounds of the general formula (Va) being particularly preferred. The above-mentioned preferred ranges apply in the same way.

The molar ratio of phosphorus to palladium in the reaction mixture can be, for example, from 1:1 to 10:1, preferably from 2:1 to 5:1, particularly preferably from 3:1 to 4:1.

In the process of the invention, the molar ratio of X to be replaced in compounds of the general formula (I) to palladium can be, for example, from 10 to 20 000; preference is given to a ratio of from 100 to 5 000, very particularly preferably from 500 to 2 000.

The process of the invention is carried out in the presence of at least one, preferably one, bulky nitrogen base.

Bulky nitrogen bases are, for example, amines of the general formula

$$NR^8R^9R^{10} \quad\quad\quad (VII)$$

where $R^8$, $R^9$ and $R^{10}$ are each, independently of one another, $C_1$–$C_{20}$-alkyl, $C_5$–$C_{14}$-aryl or $C_6$–$C_{15}$-arylalkyl or two or three of the radicals $R^8$, $R^9$ and $R^{10}$ together with the nitrogen atom may form a monocyclic, bicyclic or tricyclic heterocycle having from 4 to 8 carbon atoms per ring, with the proviso that one, two or three of the radicals $R^8$, $R^9$ and $R^{10}$, preferably two or three, are each, independently of one another, either bound to the nitrogen atom via a tertiary or quaternary $sp^3$ carbon atom or are an aryl radical which is monosubstituted or disubstituted, preferably disubstituted, in the ortho positions.

Radicals which may be bound to the nitrogen atom via a tertiary or quaternary $sp^3$ carbon atom are, by way of example and preferably, isopropyl, sec-butyl, tert-butyl, 1-methylbutyl, 1-ethylpropyl, 1,1-dimethylpropyl, 1,2-dimethylpropyl, 1-methylpentyl, 1,1-dimethylbutyl, 1,2-dimethylbutyl, 1,3-dimethylbutyl, 1-ethylbutyl, 1,1,2-trimethylpropyl, 1,2,2-trimethylpropyl, 1-ethyl-1-methylpropyl, cyclopentyl, cyclohexyl and cycloheptyl.

Aryl radicals which are monosubstituted or disubstituted in the ortho positions are, for example, o-tolyl, 2,6-dimethylphenyl, 2-ethyl-6-methylphenyl, 2,6-diisopropylphenyl, o-anisyl and 2,6-dimethoxyphenyl.

For the purposes of the invention, monocyclic heterocycles are, for example, N-methyl-2,2,6,6-tetramethylpiperidine and N-methyl-2,5-dimethylpyrrolidine.

Further bulky nitrogen bases are N-heteroaromatic compounds which are substituted in both the ortho positions relative to the nitrogen.

These are preferably 2,6-disubstituted pyridines such as 2,6-lutidine, 2,6-diethylpyridine, 2,6-diisopropylpyridine, 2,6-dimethoxypyridine, 2,6-di-tert-butylpyridine.

In the process of the invention, bulky nitrogen bases used are very particularly preferably ethyldiisopropylamine, triisopropylamine, diisopropylaniline, triisobutylamine, ethyldiisobutylamine, dicyclohexylmethylamine, cyclohexyldiethylamine, cyclohexyldimethylamine and 2,6-bis-diisopropylpyridine, among which dicyclohexylmethylamine, dicyclohexylethylamine, cyclohexyldimethylamine are particularly preferred.

The amount of base used can be, for example, from 0.2 to 200 times, preferably from 1 to 3 times and more preferably from 1.0 to 1.2 times, the molar amount of the aromatic compound of the general formula (I).

In an embodiment of the process of the invention, the bulky nitrogen base can be used in combination with another base. In this case, for example, from 1 to 95% of the amount of bulky nitrogen base can be replaced by a nonbulky nitrogen base.

Nonbulky nitrogen bases for the purposes of the invention are, for example, alkali metal and alkaline earth metal carboxylates such as acetates, propionates, benzoates, alkali metal and alkaline earth metal carbonates, hydrogencarbonates, phosphates, hydrogenphosphates, hydroxides. Alkali metals are preferably lithium, sodium, potassium and caesium, alkaline earth metals are preferably calcium, magnesium and barium.

The process of the invention is carried out in the presence of at least one, preferably one, salt.

Salts which can be used in the process of the invention are, by way of example and preferably, salts of the general formula (VIII), (Cation$^+$)(Anion$^-$) (VIII)

where
(Cation$^+$) is a substituted ammonium, phosphonium or arsonium cation or an alkali metal ion and
(Anion$^-$) is the anion of an organic or inorganic acid.
(Cation$^+$) is preferably a cation of the general formula (IX)

[Pnyc(C$_1$–C$_{12}$-alkyl)$_m$(C$_7$–C$_{12}$-arylalkyl)$_q$(C$_6$–C$_{10}$-aryl)$_r$]$^+$ (IX)

where
Pnyc is nitrogen, phosphorus or arsenic, preferably nitrogen, and
(m+q+r)=4.

(Cation$^+$) is particularly preferably tetrabutylammonium, tetraphenylammonium, tetraphenylphosphonium, tetrabutylphosphonium.

(Anion$^-$) is preferably fluoride, chloride, bromide, iodide, cyanate, thiocyanate, acetate, hydroxide, nitrate, hydrogensulphate, tetrafluoroborate, hexafluorophosphate, tosylate or triflate, particularly preferably chloride, bromide, iodide.

Very particularly preferred salts are tetrabutylammonium chloride, tetrabutylammonium bromide, tetraphenylammonium bromide, tetrabutylphosphonium chloride, tetrabutylphosphonium bromide, tetraphenylphosphonium chloride and tetraphenylphosphonium bromide, or mixtures thereof.

Particular preference is given to tetrabutylammonium bromide.

The salts can be used, for example, in amounts of 0.01–100 mol % based on the theoretical yield-limiting compound (aryl compound of the general formula (I) or the olefin), preferably in amounts of from 0.1 to 15 mol %, particularly preferably in amounts of from 0.5 to 5 mol % and very particularly preferably in amounts of from 0.5 to 2 mol %.

Larger amounts and also salt melts are possible but uneconomical.

As olefins which bear at least one hydrogen atom on the double bond, it is possible to use, for example, those of the general formula (X),

R$^{11}$CH=CR$^{12}$R$^{13}$ (X)

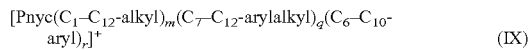

where, independently of one another,
R$^{11}$ is hydrogen or methyl and
R$^{12}$ is hydrogen or methyl and
R$^{13}$ can be hydrogen, cyano, SO$_3$M, C$_1$–C$_8$-alkyl, a carbocyclic aromatic radical having from 6 to 18 framework carbon atoms or a heteroaromatic radical having from 5 to 18 framework carbon atoms in which no, one, two or three framework carbon atoms per ring, but at least one framework carbon atom in the total molecule, may be replaced by heteroatoms selected from the group consisting of nitrogen, sulphur and oxygen
or a radical of the general formula (XI)

where

G is OM, OH, NH$_2$, OR$^{14}$, NHR$^{14}$ or N(R$^{14}$)$_2$, and R$^{14}$ is C$_1$–C$_{12}$-alkyl, C$_6$–C$_{15}$-arylalkyl or C$_5$–C$_{14}$-aryl or
the N(R$^{14}$)$_2$ moiety is a cyclic amino radical such as morpholino, pyrrolidino or piperidino, and M can be an alkali metal ion, half an equivalent of an alkaline earth metal ion, an ammonium ion or an organic ammonium ion.

The carbocyclic aromatic radicals and heteroaromatic radicals can be substituted in the same way as described under the aromatic compounds of the general formula (I).

Preferred examples of olefins of the general formula (X) are ethene, propene, butene, 1,1,1-trifluoro-2-propene, substituted or unsubstituted vinyl-C$_6$–C$_{10}$-aromatics such as styrene or the isomeric vinyinaphthalenes, 2-, 3- or 4-fluorostyrene, 2-, 3- or 4-chlorostyrene, 2-, 3- or 4-bromostyrene, 2-, 3- or 4-iodostyrene, 2-, 3- or 4-cyanostyrene, 2-, 3- or 4-(C$_1$–C$_{12}$)-alkoxystyrene such as 2-, 3- or 4-methoxystyrene, 2-, 3- or 4-nitrostyrene, 2-, 3- or 4-styrenecarboxylic acid, C$_1$–C$_{12}$-alkyl 2-, 3- or 4-styrenecarboxylates such as methyl 2-, 3- or 4-styrenecarboxylate, C$_6$–C$_{12}$-aryl 2-, 3- or 4-styrenecarboxylates such as phenyl 2-, 3- or 4-styrenecarboxylate, 2-, 3- or 4-styrenesulphonic acid or their salts, 3- or 4-vinylphthalic acid, di-C$_1$–C$_{12}$-alkyl 3- or 4-vinylphthalates such as dimethyl 3- or 4-vinylphthalate, di-C$_6$–C$_{10}$-aryl 3- or 4-vinylphthalates such as diphenyl 3- or 4-vinylphthalate, 3- or 4-vinylphthalic anhydride, vinylhetaryls such as N-vinylimidazole or 2- or 4-vinylpyridine, also acrylonitrile, acrylic acid, C$_1$–C$_{12}$-alkyl acrylates such as methyl acrylate, ethyl acrylate, n-propyl acrylate, 2-ethylhexyl acrylate, acrylamide, vinylsulphonic acid and its sulphonates.

As olefins having at least one hydrogen substituent, very particular preference is given to ethylene, propene, acrylonitrile, acrylic acid, methyl acrylate, 2-ethylhexyl acrylate, acrylamide, 1,1,1-trifluoro-2-propene and styrene, with especial preference being given to acrylonitrile, methyl acrylate, acrylamide and styrene.

The amount of olefin used can be, for example, from 0.2 to 200 times (when used as solvent) the molar amount of the aromatic compound of the general formula (I); from 0.5 to 5 times is preferred and from 0.8 to 1.2 times is very particularly preferred. Even greater preference is given to 0.9 to 1.0 times.

If aromatic compounds are of the general formula (I) or olefins of the general formula (X) which bear a free acid group such as a sulphonic acid or carboxylic acid group the amount of base used, viz. a bulky nitrogen base or nonbulky nitrogen base, has to be increased correspondingly.

If desired, the process of the invention is carried out in the presence of solvents, preferably in the presence of an aprotic solvent, particularly preferably in the presence of a dipolar aprotic solvent.

Preferred aprotic solvents are:

ethers such as dioxane, THF, 1,2-dimethoxyethane, diethylene glycol dimethyl ether, tetraethylene glycol dimethyl ether;

amide solvents such as dimethylformamide, N-methylpyrrolidone, N-methylcaprolactam or dimethylacetamide;

sulphoxides and sulphones such as dimethyl sulphoxide or tetramethylene sulphone or mixtures of such solvents;

nitriles such as acetonitrile, benzonitrile and benzyl nitrile, ketones such as dimethyl ketone, diethyl ketone, methyl tert-butyl ketone.

The amount of any solvent used can be, for example, from 50 ml to 5000 ml, preferably from 100 to 500 ml, per mol of the aromatic compound of the general formula (I).

The reaction temperature can be, for example, from 20° C. to 200° C., preferably from 80 to 150° C. and particularly preferably from 100° C. to 140° C.

The reaction can be carried out at, for example, from 0.2 to 100 bar; preference is given to atmospheric pressure.

The reaction time can be, for example, from 0.2 hour to 72 hours; preference is given to from 1 to 10 hours.

The reaction is preferably carried out under a protective gas atmosphere with substantial exclusion of oxygen and moisture. Possible protected gases are, for example, nitrogen and noble gases such as argon or mixtures of such gases.

In a preferred embodiment of the process of the invention, the aromatic compound of the general formula (I) together with the olefin, the base, the salt, the ligand and the palladium compound are placed in a reaction vessel under protective gas and the mixture is heated to the reaction temperature while stirring. After the reaction is complete, the mixture is poured into water. Solid products then precipitate and can be filtered off with suction and, for example, washed with water. Liquid products can be extracted by means of an organic solvent which is immiscible or sparingly miscible with water and be worked up, for example, by distillation.

Solid products can, if appropriate, be purified further by, for example, recrystallization or reprecipitation.

It may be advantageous to carry out the reaction under addition control by metering in the olefin at the reaction temperature during the course of the reaction.

It can be advantageous to add appropriate amounts of a free-radical inhibitor such as 2,6-di-tert-butylphenol in order to avoid secondary free-radical reactions.

Alternatively, the palladium catalyst can be added only during the course of the reaction or be generated during the course of the reaction by addition of ligand or palladium compound. The simultaneous introduction of olefins and palladium catalyst or ligand or palladium compound is also possible.

It is advantageous to use a weakly acidic aqueous solution during the work-up to bind any remaining base as salt. The base can, for example, be recovered by alkalisation and extraction of the washing liquid with an organic solvent.

The process of the invention gives arylolefins of the general formula (XII)

(XII)

where

Ar and n are as defined under the general formula (I) and $R^{11}$, $R^{12}$, $R^{13}$ are as defined under the general formula (X).

The process of the invention is particularly useful for preparing arylacrylic acid derivatives of the general formula (XIII)

(XIII)

where

Ar is as defined under the general formula (I) and $R^{11}$, $R^{12}$ are as defined under the general formula (X) and $R^{13}$ is cyano or a radical of the general formula (XI) with the meanings specified there.

The advantages of the process of the invention are the ease with which it can be carried out and the high yields of aromatic olefins. Furthermore, high catalyst turnover numbers (TONs) of above 100 mol of haloaromatic/mol of palladium catalyst and high catalyst turnover frequencies (TOFs) of above 50 per hour are achieved.

The invention is further illustrated but is not intended to be limited by the following examples in which all parts and percentages are by weight unless otherwise specified.

EXAMPLES

Example 1

Synthesis of 3-trifluoromethylcinnamide (method I)

0.512 g (7.2 mmol) of acrylamide, 38.7 mg (120 μmol) of NBu$_4$Br, 6.7 mg (30 μmol) of palladium acetate and 26.7 mg (120 μmol) of phenyldi(t-butyl)phosphine are weighed into a Schlenk vessel. 1.08 g (6 mmol) of 3-chlorobenzotrifluoride and 1.53 ml (7.2 mmol) of dicyclohexylmethylamine and also 3.5 ml of dimethylacetamide are then added. The Schlenk vessel is placed in a heating bath at 120° C. and the contents are stirred. After 4 hours, the contents are poured into 30 ml of water and the product is extracted by shaking with t-butyl methyl ether. After drying the organic phase over MgSO$_4$, the solvent is removed under reduced pressure and the product is isolated. Yellowish oil, yield: 917 mg (71% of theory).

Example 2

Synthesis of 3-trifluoromethylcinnamide (method II)

0.181 g (2.55 mmol) of acrylamide, 9.7 mg (30 μmol) of NBu$_4$Br, 0.675 mg (3 μmol) of palladium acetate and 2.67 mg (12 μmol) of phenyldi(t-butyl)phosphine are weighed into a Schlenk vessel. 0.542 g (3 mmol) of 3-chlorobenzotrifluoride and 0.637 ml (3 mmol) of dicyclohexylmethylamine and also 2.5 ml of dimethylacetamide are then added. The Schlenk vessel is placed in a heating bath at 130° C. and the contents are stirred. After 3 hours, the yield is determined by means of HPLC: 64% (TON=544, TOF=181/h).

Example 3

Synthesis of 4-trifluoromethylcinnamide (method I)

0.512 g (7.2 mmol) of acrylamide, 23.2 mg (72 μmol) of NBu$_4$Br, 3.2 mg (14.4 μmol) of palladium acetate and 12.8 mg (58 μmol) of phenyldi(t-butyl)phosphine are weighed into a Schlenk vessel. 1.56 g (8.63 mmol) of 4-chlorobenzotrifluoride and 1.83 ml (8.63 mmol) of dicyclohexylmethylamine and also 4 ml of dimethylacetamide are then added. The Schlenk vessel is placed in a heating bath at 110° C. and the contents are stirred. After 24 hours, the contents are poured into 30 ml of water, the solid product is filtered off with suction and washed with about 50 ml of water. Colorless solid, yield after drying: 1.47 g (94.8% of theory).

Example 4

Synthesis of 4-trifluoromethylcinnamide (method II)

As Example 3, but only 1.6 mg (7.2 µmol) of palladium acetate and 6.4 mg (29 µmol) of phenyldi(t-butyl)phosphine were used. In this example, the reaction temperature was increased to 120° C. and a yield of 1.36 g (88% of theory; TON=880; TOF=220/h) was obtained after only 4 hours.

Example 5

Synthesis of 4-trifluoromethylcinnamide (method III)

0.178 g (2.5 mmol) of acrylamide, 10 mg (30 µmol) of NBu$_4$Br, 1.2 mg (6 µmol) of palladium acetate and 4.8 mg (24 µmol) of phenyldi(t-butyl)phosphine are weighed into a Schlenk vessel. 0.541 g (3 mmol) of 4-chlorobenzotrifluoride and 0.754 g (3.6 mmol) of dicyclohexylethylamine and also 2 ml of dimethylacetamide are then added. The Schlenk vessel is placed in a heating bath at 130° C. and the contents are stirred. After 4 hours, 200 µl of the reaction solution are taken out and diluted with 3.8 ml of methyl-tert.-butyl-ether. The sample is then analyzed by means of HPLC. Yield: 100% of the desired product.

Example 6

Synthesis of 4-trifluoromethylcinnamide (method IV)

0.178 g (2.5 mmol) of acrylamide, 10 mg (30 µmol) of NBu$_4$Br, 1.2 mg (6 µmol) of palladium acetate and 4.8 mg (24 µmol) of phenyldi(t-butyl)phosphine are weighed into a Schlenk vessel. 0.541 g (3 mmol) of 4-chlorobenzotrifluoride and 0.559 g (3.6 mmol) of cyclohexyldiethylamine and also 2 ml of dimethylacetamide are then added. The Schlenk vessel is placed in a heating bath at 130° C. and the contents are stirred. After 4 hours, 200 µl of the reaction solution are taken out and diluted with 3.8 ml of methyl-tert.-butyl-ether. The sample is then analyzed by means of HPLC. Yield: 100% of the desired product.

Example 7

Synthesis of 4-trifluoromethylcinnamide (method V)

0.178 g (2.5 mmol) of acrylamide, 10 mg (30 µmol) of NBu$_4$Br, 1.2 mg (6 µmol) of palladium acetate and 4.8 mg (24 µmol) of phenyldi(t-butyl)phosphine are weighed into a Schlenk vessel. 0.541 g (3 mmol) of 4-chlorobenzotrifluoride and 0.458 g (3.6 mmol) of cyclohexyldimethylamine and also 2 ml of dimethylacetamide are then added. The Schlenk vessel is placed in a heating bath at 130° C. and the contents are stirred. After 4 hours, 200 µl of the reaction solution are taken out and diluted with 3.8 ml of methyl-tert.-butyl-ether. The sample is then analyzed by means of HPLC. Yield: 100% of the desired product.

Example 8

Synthesis of 4-trifluoromethylcinnamide (method VI)

0.178 g (2.5 mmol) of acrylamide, 10 mg (30 µmol) of NBu$_4$Br, 1.2 mg (6 µmol) of palladium acetate and 4.8 mg (24 µmol) of phenyldi(t-butyl)phosphine are weighed into a Schlenk vessel. 0.541 g (3 mmol) of 4-chlorobenzotrifluoride and 0.465 g (3.6 mmol) of ethyldiisopropylamine and also 2 ml of dimethylacetamide are then added. The Schlenk vessel is placed in a heating bath at 130° C. and the contents are stirred. After 4 hours, 200 µl of the reaction solution are taken out and diluted with 3.8 ml of methyl-tert.-butyl-ether. The sample is then analyzed by means of HPLC. Yield: 96% of the desired product.

Example 9

Synthesis of 3,5-bis(trifluoromethyl)cinnamide (method I)

0.512 g (7.2 µmol) of acrylamide, 38.7 mg (120 µmol) of NBu$_4$Br, 6.7 mg (30 µmol) of palladium acetate and 26.7 mg (120 µmol) of phenyldi(t-butyl)phosphine are weighed into a Schlenk vessel. 1.49 g (6 mmol) of 3,5-bis(trifluoromethyl)chlorobenzene and 1.53 ml (7.2 mmol) of dicyclohexylmethylamine and also 3.5 ml of dimethylacetamide are then added. The Schlenk vessel is placed in a heating bath at 130° C. and the contents are stirred. After 4 hours, the contents are poured into 30 ml of water, the solid product is filtered off with suction and washed with about 50 ml of water. Light-grey solid, yield after drying: 1.63 g (96% of theory).

Example 10

Synthesis of 3,5-bis(trifluoromethyl)cinnamide (method II)

0.181 g (2.55 mmol) of acrylamide, 9.7 mg (30 µmol) of NBu$_4$Br, 0.675 mg (3 µmol) of palladium acetate and 2.67 mg (12 µmol) of phenyldi(t-butyl)phosphine are weighed into a Schlenk vessel. 0.542 g (3 mmol) of 3,5-bis(trifluoromethyl)chlorobenzene and 0.637 ml (3 mmol) of dicyclohexylmethylamine and also 2.5 ml of dimethylacetamide are then added. The Schlenk vessel is placed in a heating bath at 130° C. and the contents are stirred. After 3 hours, the yield is determined by means of HPLC: 99% (TON=723, TOF=241/h).

Example 11

Synthesis of 3-cyano-4-trifluoromethylcinnamide 0.512 g (7.2 mmol) of acrylamide, 38.7 mg (120 µmol) of NBu$_4$Br, 6.7 mg (30 µmol) of palladium acetate and 26.7 mg (120 µmol) of phenyldi(t-butyl)phosphine are weighed into a Schlenk vessel. 1.23 g (6 mmol) of 3-cyano-4-trifluoromethylchlorobenzene and 1.53 ml (7.2 mmol) of dicyclohexylmethylamine and also 3.5 ml of dimethylacetamide are then added. The Schlenk vessel is placed in a heating bath at 130° C. and the contents are stirred. After 4 hours, the contents are poured into 30 ml of water, the solid product is filtered off with suction and washed with about 50 ml of water. Light-grey solid, yield after drying: 1.26 g (87% of theory).

Example 12

Synthesis of 3-methyl-4-trifluoromethylcinnamide 0.512 g (7.2 mmol) of acrylamide, 38.7 mg (120 µmol) of NBu$_4$Br, 6.7 mg (30 µmol) of palladium acetate and 26.7 mg (120 µmol) of phenyldi(t-butyl)phosphine are weighed into a Schlenk vessel. 1.17 g (6 mmol) of 3-methyl-4-trifluoromethylchlorobenzene and 1.53 ml (7.2 mmol) of dicyclohexylmethylamine and also 3.5 ml of dimethylacetamide are then added. The Schlenk vessel is placed in a heating bath at 130° C. and the contents are stirred. After 4 hours, the contents are poured into 30 ml of water, the solid product is filtered off with suction and washed with about 30 ml of water. Light-grey solid, yield after drying: 1.29 g (92.8% of theory).

Example 13

Synthesis of methyl 3,5-bis(trifluoromethyl)cinnamate 0.619 g (7.2 mmol) of methyl acrylate, 38.7 mg (120 µmol) of NBu$_4$Br, 6.7 mg (30 µmol) of palladium acetate and 26.7 mg (120 µmol) of phenyldi(t-butyl)phosphine are weighed into a Schlenk vessel. 1.49 g (6 mmol) of 3,5-bis(trifluoromethyl)chlorobenzene and 1.53 ml (7.2 mmol) of dicyclohexylmethylamine and also 3.5 ml of dimethylacetamide are then added. The Schlenk vessel is placed in a heating bath at 130° C. and the contents are stirred. After 4 hours, the contents are poured into 30 ml of water and the product is extracted by shaking with t-butyl methyl ether. After drying the organic phase over MgSO$_4$, the solvent is removed under reduced pressure and the product is isolated. Yellowish, crystalline solid, yield: 1.34 g (97% of theory).

Example 14

Synthesis of methyl 3-cyano-4-trifluoromethylcinnamate 0.619 g (7.2 mmol) of methyl acrylate, 38.7 mg (120 µmol) of NBu$_4$Br, 6.7 mg (30 µmol) of palladium acetate and 26.7 mg (120 µmol) of phenyldi(t-butyl)phosphine are weighed into a Schlenk vessel. 1.23 g (6 mmol) of 3-cyano-4-trifluoromethylchlorobenzene and 1.53 ml (7.2 mmol) of dicyclohexylmethylamine and also 3.5 ml of dimethylacetamide are then added. The Schlenk vessel is placed in a heating bath at 130° C. and the contents are stirred. After 4 hours, the contents are poured into 30 ml of water and the product is extracted by shaking with t-butyl methyl ether. After drying the organic phase over MgSO$_4$, the solvent is removed under reduced pressure and the product is isolated. Yellowish, crystalline solid, yield: 1.31 g (85.5% of theory).

Example 15

Synthesis of methyl 3-methyl-4-trifluoromethylcinnamate 0.619 g (7.2 mmol) of methyl acrylate, 38.7 mg (120 µmol) of NBu$_4$Br, 6.7 mg (30 µmol) of palladium acetate and 26.7 mg (120 µmol) of phenyldi(t-butyl)phosphine are weighed into a Schlenk vessel. 1.17 g (6 mmol) of 3-methyl-4-trifluoromethylchlorobenzene and 1.53 ml (7.2 mmol) of dicyclohexylmethylamine and also 3.5 ml of dimethylacetamide are then added. The Schlenk vessel is placed in a heating bath at 130° C. and the contents are stirred. After 4 hours, the contents are poured into 30 ml of water and the product is extracted by shaking with t-butyl methyl ether. After drying the organic phase over MgSO$_4$, the solvent is removed under reduced pressure and the product is isolated. Yellowish, crystalline solid. Yield: 86%, two products in a ratio of 99:1 (trans/cis products).

Example 16

Synthesis of 3,5-bis(trifluoromethyl)cinnamonitrile 0.382 g (7.2 mmol) of acrylonitrile, 38.7 mg (120 µmol) of NBu$_4$Br, 6.7 mg (30 µmol) of palladium acetate and 26.7 mg (120 µmol) of phenyldi(t-butyl)phosphine are weighed into a Schlenk vessel. 1.49 g (6 mmol) of 3,5-bis(trifluoromethyl)chlorobenzene and 1.53 ml (7.2 mmol) of dicyclohexylmethylamine and also 3.5 ml of dimethylacetamide are then added. The Schlenk vessel is placed in a heating bath at 130° C. and the contents are stirred. After 4 hours, the contents are poured into 30 ml of water and the product is extracted by shaking with t-butyl methyl ether. After drying the organic phase over MgSO$_4$, the solvent is removed under reduced pressure and the product is isolated. Orange oil, yield: 69%.

Example 17

Synthesis of 3-trifluoromethyl-trans-stilbene 0.745 g (7.2 mmol) of styrene, 38.7 mg (120 µmol) of NBu$_4$Br, 6.7 mg (30 µmol) of palladium acetate and 26.7 mg (120 µmol) of phenyldi(t-butyl)phosphine are weighed into a Schlenk vessel. 1.08 g (6 mmol) of 3-chlorobenzotrifluoride and 1.53 ml (7.2 mmol) of dicyclohexylmethylamine and also 3.5 ml of dimethylacetamide are then added. The Schlenk vessel is placed in a heating bath at 130° C. and the contents are stirred. After 4 hours, the contents are poured into 30 ml of water and the product is extracted by shaking with t-butyl methyl ether. After drying the organic phase over MgSO$_4$, the solvent is removed under reduced pressure and the product is isolated. Yellowish, crystalline solid, yield: 1.43 g (96% of theory).

Example 18

Synthesis of 4-methoxyphenylcinnamide 0.181 g (2.55 mmol) of acrylamide, 9.7 mg (30 µmol) of NBu$_4$Br, 0.068 mg (0.3 µmol) of palladium acetate and 0.27 mg (1.2 µmol) of phenyldi(t-butyl)phosphine are weighed into a Schlenk vessel. 0.561 g (3 mmol) of 4-bromoanisole and 0.637 ml (3 mmol) of dicyclohexylmethylamine and also 2.5 ml of dimethylacetamide are then added. The Schlenk vessel is placed in a heating bath at 130° C. and the contents are stirred. After 3 hours, the yield is determined by means of HPLC: 100% yield (TON=8500, TOF=2833/h); two isomeric products in a ratio of 61/39.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for preparing arylolefins, comprising reacting aromatic compounds of the general formula (I), $$Ar—[X]_n \quad (I),$$

where
n is one or two and
Ar is a substituted or unsubstituted aromatic radical and
X are each, independently of one another, chlorine, bromine, iodine or a sulphonate,
with olefins which bear at least one hydrogen atom on the double bond in the presence of a palladium catalyst, at least one bulky nitrogen base and at least one salt; wherein
(a) the aromatic radical is a substituted or unsubstituted carbocyclic radical having from 6 to 24 carbon atoms;
(b) the at least one bulky nitrogen base is or are selected from the group consisting of ethyldiisopropylamine, triisopropylamine, diisopropylaniline, triisobutylamine, ethyldiisobutylamine, dicyclohexylmethylamine, dicyclohexylethylamine, cyclohexyldiethylamine, oyclohexyldimethylamine and bis(diisopropyl)pyridine, and combinations thereof;
(c) the salt comprises an ammonium, phosphonium, arsonium or alkali metal cation,
(d) the palladium catalyst is a palladium complex prepared with the following phosphorus compounds:
   1. tri(tert-butyl)phosphine
   2. phenyl di(tert-butyl)phosphine
   3. ferrocenyldi(tert-butyl)phosphine.

2. Process according to claim 1, wherein the reaction is carried out in the presence of solvents.

3. Process according to claim 1, wherein the reaction is carried out in the presence of a dipolar aprotic solvent.

4. Process according to claim 1, wherein the arylolefins are of the general formula (I), where
Ar is a carbocyclic aromatic radical having from 6 to 24 framework carbon atoms or a heteroaromatic radical having from 5 to 24 framework carbon atoms in which no, one, two or three framework carbon atoms per ring, but at least one framework carbon atom in the total molecule, is/are replaced by heteroatoms selected from the group consisting of nitrogen, sulphur and oxygen, where
the carbocyclic aromatic radical or heteroaromatic radical is substituted by up to five identical or different substituents per ring selected from the group consisting of hydroxy, fluoro, nitro, cyano, free or protected formyl, $C_1$–$C_{12}$-alkyl, $C_5$–$C_{14}$-aryl, $C_6$–$C_{15}$-arylalkyl, —PO—[($C_1$–$C_8$)-alkyl]$_2$, —PO—[($C_5$–$C_{14}$)-aryl]$_2$, —PO—[($C_1$–$C_8$)-alkyl]($C_5$–$C_{14}$-aryl], tri($C_1$–$C_8$-alkyl)siloxyl and radicals of the general formula (II), $$A\text{-}B\text{-}D\text{-}E \quad (II)$$

where, independently of one another,
A is absent or is a $C_1$–$C_8$-alkylene radical and
B is absent or is oxygen, sulphur or $NR^1$, where $R^1$ is hydrogen, $C_1$–$C_8$-alkyl, $C_6$–$C_{15}$-arylalkyl or $C_5$–$C_{14}$-aryl,
D is a carbonyl group and
E is $R^2$, $OR^2$, $NHR^3$ or $NR(R^3)_2$,
where $R^2$ is $C_1$–$C_8$-alkyl, $C_6$–$C_{15}$-arylalkyl, $C_1$–$C_8$-haloalkyl or $C_5$–$C_{14}$-aryl and
$R^3$ are each, independently of one another, $C_1$–$C_8$-alkyl, $C_6$–$C_{15}$-arylalkyl or $C_6$–$C_{14}$-aryl or the moiety $N(R^3)_2$ is a cyclic amino radical, and radicals of the general formulae (IIIa–e)

| | |
|---|---|
| A-E | (IIIa) |
| A-SO$_2$-E | (IIIb) |
| A-B-SO$_2$R$^2$ | (IIIc) |
| A-SO$_3$W | (IIId) |
| A-COW | (IIIe) | where A, B, E and $R^2$ are as defined above and W is OH, $NH_2$, or OM, where M is an alkali metal ion, half an equivalent of an alkaline earth metal ion, an ammonium ion or an organic ammonium ion and
X is chlorine, bromine, iodine, trifluoromethanesulphonyloxy or nonafluorobutanesulphonyloxy.

5. Process according to claim 1, wherein the aromatic compounds used are compounds of the general formula (I) in which
n=one and
Ar is a substituted or unsubstituted aromatic radical selected from the group consisting of phenyl, naphthyl, phenanthrenyl, anthracenyl, fluorenyl, pyridinyl, oxazolyl, thiophenyl, benzofuranyl, benzothiophenyl, dibenzofuranyl, dibenzothiophenyl, furanyl, indolyl, pyridazinyl, pyrazinyl, pyrimidinyl, triazolyl and quinolinyl, optionally substituted by no, one, two or three radicals per ring which are selected independently from the group consisting of fluorine, nitro, cyano, di($C_1$–$C_6$-alkyl)amino, $C_1$–$C_6$-alkyl, $C_6$–$C_{14}$-aryl, $C_1$–$C_8$-fluoroalkyl, $C_1$–$C_8$-fluoroalkoxy, $C_1$–$C_8$-alkoxy, CO($C_1$–$C_4$-alkyl), COO—($C_1$–$C_4$-alkyl), —CON($C_{11}$–$C_6$-alkyl)$_2$, and
X is chlorine, bromine, iodine, trifluoromethanesulphonyloxy or nonafluorobutanesulphonyloxy.

6. Process according to claim 1, wherein, in the general formula (I),
X is chlorine.

7. Process according to claim 1, wherein the palladium catalysts used are palladium complexes.

8. Process according to claim 1, wherein the palladium catalysts used are palladium complexes which are generated in the reaction solution from palladium compounds and phosphorus compounds.

9. Process according to claim 8, wherein the phosphorus compounds used are mono phosphorus compounds of the general formula (Va), $$P(E\text{-}R^4)_3 \quad (Va)$$

where
E are each, independently of one another and independently of $R^4$, absent or oxygen and the radicals $R^4$ are each, independently of one another, $C_1$–$C_8$-alkyl or unsubstituted phenyl, naphthyl or ferrocenyl or phenyl, naphthyl or ferrocenyl substituted by one, two or three radicals $R^5$, where
$R^5$ is $C_1$–$C_8$-alkyl, $C_1$–$C_8$-alkoxy, chlorine, fluorine, $N(C_1$–$C_6$-alkyl)$_2$, $CO_2$—($C_1$–$C_6$-alkyl), —CON($C_1$–$C_6$-alkyl)$_2$, cyano or CO($C_1$–$C_6$-alkyl) or diphosphorus compounds of the general formula (Vb), $$(R^6\text{-}E)_2P\text{-}E\text{-}Z\text{-}E\text{-}P(E\text{-}R^8)_2 \quad (Vb)$$

where
- E are each, independently of one another and independently of $R^6$ and Z, absent or oxygen and
  the radicals $R^6$ are each, independently of one another, $C_1$–$C_8$-alkyl or phenyl, naphthyl or heteroaryl having from 5 to 12 framework carbon atoms which may be unsubstituted or substituted by one, two or three radicals $R^7$, where
  $R^7$ are selected independently from the group consisting of $C_1$–$C_8$-alkyl, $C_1$–$C_8$-alkoxy, fluorine and cyano and
- Z is an unsubstituted or substituted radical selected from the group consisting of $C_1$–$C_4$-alkylene, 1,2-phenylene, 1,3-phenylene, 1,2-cyclohexylene, 1,1'-ferrocenylene, 1,2-ferrocenylene, 2,2'-(1,1'-binaphthylene) and 1,1'-biphenylene.

10. Process according to claim 5, wherein phosphorus compounds used are tri(tert-butyl)phosphine, phenyldi(tert-butyl)phosphine or ferrocenyldi(tert-butyl)phosphine.

11. Process according to claim 8, wherein the molar ratio of phosphorus to palladium in the reaction mixture is from 1:1 to 10:1.

12. Process according to claim 11, wherein the molar ratio of phosphorus to palladium in the reaction mixture is from 3:1 to 4:1.

13. Process according to claim 1, wherein the molar ratio of X in compounds of the general formula (I) to palladium is from 10 to 20 000.

14. Process according to claim 1, wherein the bulky nitrogen bases used are amines of the general formula, $$NR^8R^9R^{10} \quad (VII)$$

where
- $R^8$, $R^9$ and $R^{10}$ are each, independently of one another, $C_1$–$C_{20}$-alkyl, $C_5$–$C_{14}$-aryl or $C_6$–$C_{15}$-arylalkyl or two or three of the radicals $R^8$, $R^9$ and $R^{10}$ together with the nitrogen atom may form a monocyclic, bicyclic or tricyclic heterocycle having from 4 to 8 carbon atoms per ring,
- with the proviso that one, two or three of the radicals $R^8$, $R^9$ and $R^{10}$ are each, independently of one another, either bound to the nitrogen atom via a tertiary or quaternary sp$^3$ carbon atom or are an aryl radical which is monosubstituted or disubstituted in the ortho positions or N-heteroaromatic compounds which are substituted in the two ortho positions relative to the nitrogen.

15. Process according to claim 14, with the proviso that two or three of the radicals $R^8$, $R^9$ and $R^{10}$ of the amines of formula (VII) are each, independently of one another, either bound to the nitrogen atom via a tertiary or quaternary sp$^3$ carbon atom or are an aryl radical which is monosubstituted or disubstituted in the ortho positions or N-heteroaromatic compounds which are substituted in the two ortho positions relative to the nitrogen.

16. Process according to claim 1, wherein bulky nitrogen bases used are ethyldiisopropylamine, triisopropylamine, diisopropylaniline, triisobutylamine, ethyldiisobutylamine, dicyclohexylmethylamine, dicyclohexylethylamine, cyclohexyldiethylamine, cyclohexyldimethylamine and bis(diisopropyl)pyridine.

17. Process according to claim 1, wherein salts used are ones of the general formula (VIII), $$(Cation^+)(Anion^-) \quad (VIII)$$

where
- (Cation$^+$) is a substituted ammonium, phosphonium or arsonium cation or an alkali metal ion, and
- (Anion$^-$) is the anion of an organic or inorganic acid.

18. Process according to claim 1, wherein salts used are tetrabutylammonium chloride, tetrabutylammonium bromide, tetraphenylammonium bromide, tetrabutylphosphonium chloride, tetrabutylphosphonium bromide, tetraphenylphosphonium chloride, tetraphenylphosphonium bromide or mixtures thereof.

19. Process according to claim 1, wherein the salts are used in amounts of 0.5–2 mol % based on the theoretical yield-limiting compound.

20. Process according to claim 1, wherein the olefins bearing at least one hydrogen atom on the double bond are olefins of the general formula (X), $$R^{11}CH=CH^{12}R^{13} \quad (X)$$

where, independently of one another,
- $R^{11}$ is hydrogen or methyl and
- $R^{12}$ is hydrogen or methyl and
- $R^{13}$ is hydrogen, cyano, $SO_3M$, $C_1$–$C_8$-alkyl, a carbocyclic aromatic radical having from 6 to 18 framework carbon atoms or a heteroaromatic radical having from 5 to 18 framework carbon atoms in which no, one, two or three framework carbon atoms per ring, but at least one framework carbon atom in the total molecule, is optionally replaced by heteroatoms selected from the group consisting of nitrogen, sulphur and oxygen or a radical of the general formula (XI)

(XI)

where
- G is OM, OH, $NH_2$, $OR^{14}$, $NHR^{14}$ or $N(R^{14})_2$, and $R^{14}$ is $C_1$–$C_{12}$-alkyl, $C_6$–$C_{15}$-arylalkyl or $C_6$–$C_{10}$-aryl or
- the $N(R^{14})_2$, and M is an alkali metal ion, half an equivalent of an alkaline earth metal ion, an ammonium ion or an organic ammonium ion is a cyclic amino radical.

21. Process according to claim 1, wherein the olefins having at least one hydrogen substituent are selected from the group consisting of ethylene, propene, acrylonitrile, acrylic acid, methyl acrylate, 2-ethylhexyl acrylate, acrylamide, 1,1,1-trifluoro-2-propene and styrene.

22. Process according to claim 1, wherein the olefins having at least one hydrogen substituent which are used are acrylonitrile, methyl acrylate, acrylamide, or styrene.

23. Process according to claim 1, wherein the reaction temperature is from 20° C. to 200° C.

* * * * *